United States Patent [19]

Takai et al.

[11] Patent Number: 4,945,895
[45] Date of Patent: Aug. 7, 1990

[54] REMOTE FIBER OPTIC MEDICAL PROCEDURE AND DEVICE

[75] Inventors: Kazuo Takai, Tokyo; Scott Genty, Kanagawa, both of Japan; Frederick D. Roemer, Bloomington, Ind.

[73] Assignee: Vance Products Incorporated, Spencer, Ind.

[21] Appl. No.: 326,011

[22] Filed: Mar. 20, 1989

[51] Int. Cl.⁵ ............................. A61B 1/06; A61B 17/34
[52] U.S. Cl. .......................................... 128/6; 606/170
[58] Field of Search ................ 128/4, 6, 7; 606/167, 606/170

[56] References Cited

U.S. PATENT DOCUMENTS

| | | | |
|---|---|---|---|
| 1,620,828 | 3/1927 | Molony | 128/6 |
| 3,349,762 | 10/1967 | Kapany | 128/6 X |
| 3,556,085 | 1/1971 | Takahashi | 128/6 |
| 3,941,121 | 3/1976 | Olinger et al. | 128/6 |
| 3,961,621 | 6/1976 | Northeved | 128/6 X |
| 4,269,192 | 5/1981 | Matsuo | 128/6 X |
| 4,539,976 | 9/1985 | Sharpe | 128/6 |
| 4,566,438 | 1/1986 | Liese et al. | 128/6 |
| 4,607,622 | 8/1986 | Fritch et al. | 128/6 |
| 4,736,733 | 4/1988 | Adair | 128/6 |
| 4,742,819 | 5/1988 | George | 128/6 |
| 4,756,303 | 7/1988 | Kawashima et al. | 128/6 |
| 4,878,487 | 11/1989 | Sinnett | 128/6 X |

Primary Examiner—William H. Grieb
Attorney, Agent, or Firm—Woodard, Emhardt, Naughton, Moriarty & McNett

[57] ABSTRACT

A medical procedure involving direction of the operative end of a medical instrument via observation through a remote small caliber fiber optic bundle disposed through a prepositioned needle lumen.

25 Claims, 4 Drawing Sheets

REMOTE FIBER OPTIC MEDICAL PROCEDURE AND DEVICE

BACKGROUND OF THE INVENTION

1. Field of the Invention

This invention relates generally to endoscopic procedures and medical devices useful in such procedures and more particularly to an endoscopic procedure wherein a small caliber fiber optic bundle is used to remotely view the operative end of a catheter.

2. Brief Description of the Background

When performing endoscopic procedures, it is necessary to place the operative end of the endoscope in proper relation to the target body tissue so that the desired medical procedure may be performed. It is necessary, therefore, that some means be available by which to observe such operative part, thus enabling guidance to the part of the body Where medical intervention is required.

Commonly, endoscopes have fiber optic bundles disposed through one channel of the endoscope. A portion of the fibers transmit light to the internal body cavity. The clinician views internally by way of return (or image forming) light which passes through some amplification device, often an adapted magnifying lens. In this manner, the clinician may directly view the collected image.

This arrangement of a fiber optic bundle within an endoscope has several disadvantages. The ability to position the endoscope is impaired since the field of vision is limited to internal features in the path of the endoscope's distal end. A primary drawback is, then, that the operative end of the endoscope may not be visible because it is behind or beside the field of vision from the fiber optic bundle. When more than one operative medical device is disposed within a multi-lumen endoscope, placement of any one of such devices may be further complicated. For example, if one lumen of the endoscope contains a grasping forcep while another contains a loop retrieval wire, the physician may expend a great deal of effort as he determines the exact position of the desired operative device needed to perform the medical procedure. There is also a potential that the two devices may become entangled.

The relatively extended position of the operative end is nearly impossible to determine in the commonly used endoscope. Even if the operative end is visible, the depth relationship between it and other instruments or the body tissues is indeterminate since the field of vision is parallel with the operative end. The image observed by the physician cannot accurately relay depth information since such linear observations are inherently two-dimensional. In other words, this operative end may be in various positions of relative extension or retraction, which positions may remain undetectable through the common endoscope until actual contact with the body tissue is achieved. Thus when placing the endoscope for effective treatment or diagnosis, the clinician must use some guesswork to avoid damaging tissue or missing the target.

Another disadvantage of endoscopic procedures wherein the endoscope contains the fiber optic bundle is that the diameter of the endoscope must be large enough to accommodate the fiber optic bundle. This creates impediments to effective medical procedure. First, the trauma experienced with advancing an endoscope, either through existing anatomical ducts or percutaneously, increases with increased endoscope size. Also, larger endoscopes are less deflectable.

Another common medical procedure employs a catheter without a fiber optic bundle disposed within one of its lumens. The catheter is advanced into the body cavity toward the target tissue under external guidance. For example, the endoscope may be advanced to the ultimate location using x-ray (fluoroscopic) or ultrasound guidance. This method of indirectly positioning a catheter has disadvantages. Great interpretive skill may be required to correctly position and manipulate the operative tip, since the returned visual imagery is an indirect representation of the actual internal cavity.

The endoscopic procedure of the present invention overcomes these disadvantages in present medical procedures. It allows real image visualization of the operative tip of an advancing catheter as that advancement relates to the target tissue. Since the fiber optic bundle is removed from the catheter, the catheter's diameter may he decreased or alternatively, its functionality may be increased. Should the diameter be decreased, the catheter becomes actively deflectable. Moreover, the present procedure is atraumatic as compared to percutaneous access in certain endoscopic procedures presently in use where the endoscopic access is through punctures.

Various medical devices using fiber optics have been developed, none of which disclose the principles of the present invention.

Northeved U.S. Pat. No. 3,961,621, discloses a device comprised of an elongated bevel cut needle with a tubular stiletto disposed therein capable of taking biological samples from a human body. Fiber optic bundles are disposed in parallel with and circumferentially of the stiletto for use in guiding the stiletto to the target tissue. A vacuum may be applied through fine air ducts alternately disposed with the fiber optic bundles.

Matsuo, U.S. Pat. No. 4,269,192, discloses a medical instrument comprising a tubular member which has a bevel cut end. The intensity of light emitted into the body and then reflected from the examination area activates an LED which signals the intensity of the reflected light indicating the location of the operative end of the instrument. The fiber optics are disposed axially within the operative tubular member.

Takahashi, U.S. Pat. No. 3,556,085, discloses a microscope adapted for insertion into the human body comprising a bevel cut fiber optic system and incorporating magnifying objective lenses and an eye piece. The lens system is variously positionable to achieve different levels of magnification. The microscope is designed for use with with an operative medical instrument disposed in parallel with the fiber optics and in the same housing.

Olinger, U.S. Pat. No. 3,941,121, discloses a small caliber endoscope including a hollow needle with a lens system and image transmitting fiber optic bundle within the needle. A channel for receiving an operative medical instrument, specifically an electrode for stimulating spinal nerves, is provided. The operative channel is disposed longitudinally parallel with the fiber optic bundle.

Kapany,. U.S. Pat. No. 3,349,762, discloses a medical instrument for measuring blood flow velocity using fiber optics to determine the intensity of the light transmitted by flowing blood. The intensity is measured by a photocell and converted to an analog voltage or current output.

Liese, U.S. Pat. No. 4,566,438, discloses a stylet incorporating fiber optic bundles to return the intensity and color of reflected light in order to localize a needle tip. The fiber optics are beveled at one end and the encasement is closed with a low vapor pressure epoxy. The receiving fiber has a reflective surface adjacent to the beveled end of the instrument.

None of these patents disclose a medical procedure wherein a very small fiber optic bundle is inserted through the lumen of a prepositioned needle in order to remotely direct the operative tip of another medical instrument via direct visualization of instrument's operative tip.

SUMMARY OF THE INVENTION

One embodiment of the present invention is a method wherein a multi-lumen catheter is partially advanced through existing anatomical ducts, a needle with an obturating stylet axially disposed within is inserted percutaneously at some angle facilitating sight of the catheter's distal end, the stylet is then removed and a fiber optic bundle inserted through the needle lumen, followed by catheter advancement to the target tissue via direct visualization from the fiber optics. One embodiment of a medical instrument combination made according to the present invention is a small caliber needle through which a removable obturating stylet is disposed. Once the needle is percutaneously placed the stylet is removed and a fiber optic bundle is then inserted through the needle's lumen in order to visualize the advancement of a multi-lumen catheter. An alternative embodiment is connection of the fiber optic bundle to a cathode ray tube or a television screen for real image visualization of the catheter.

It is an object of the present invention to provide an improved method for positioning and operating a catheter with respect to target body tissue.

It is another object to provide a medical instrument for achieving the method described above.

It is a further object of the present invention to provide a new and improved fiber optic assembly which incorporates a television or other display screen to determine the location of a remote surgical instrument within the body.

Still a further object of the present invention is to provide an endoscopic procedure Wherein the operative tip is actively deflectable.

A further object of the present invention is to provide an improved access instrument which may be percutaneously inserted atraumatically.

Further objects and advantages will be become apparent from the folloWing description.

BRIEF DESCRIPTION OF THE DRAWINGS

FIGS. 4b through 4e are fractional views of the section shown in FIG. 4a taken upward of line b—b.

FIG. 4a shows a multi-lumen catheter partially advanced through the ureter toward a kidney stone.

FIG. 4b shows the catheter of FIG. 4a further advanced and into the renal pelvis and a needle with an obturating stylet disposed therein percutaneously inserted into the collecting system of the kidney.

FIG. 4c shows the obturating stylet of FIG. 4b partially removed from the needle's lumen.

FIG. 4d illustrates the needle of FIG. 4c with the obturating stylet completely removed and a fiber optic bundle inserted through the needle's lumen into the kidney so that the position of the catheter relative the kidney stone is observable.

FIG. 4e shows the catheter after advancement aided by observation through the fiber optic bundle with the catheter at the site of the kidney stone.

DETAILED DESCRIPTION OF THE PREFERRED EMBODIMENT

Figure 1:
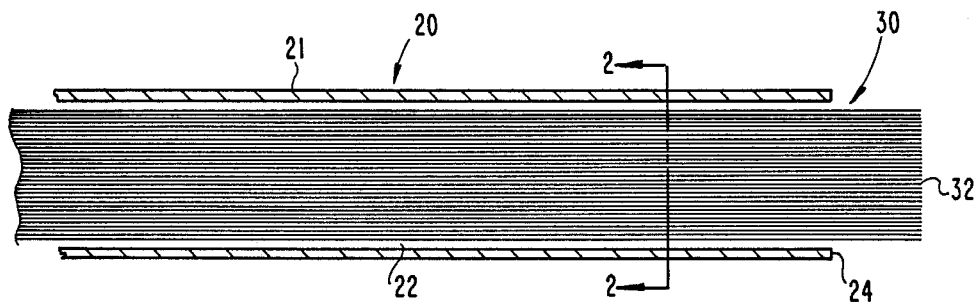
FIG. 1 is an enlarged, fragmentary, longitudinal, cross-sectional view showing the distal portion of a needle with a fiber optic bundle disposed therein, and useful in practicing the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Turning now to the drawings in detail, FIG. 1 shows a partial cross-section of a needle 20 through which a fiber optic bundle 30 has been inserted. The distal tip 32 of the fiber optic bundle 30 is extendable beyond the distal tip 24 of the needle 20. An obturating stylet (not shown) inserted through the lumen 22 of the needle 20 is used for initial puncture and positioning. Preferably, this needle has an 18 gauge (0.049 inch) or less outer diameter and a lumen 22 diameter of 0.039 inches or less. The needle 20 and fiber optic bundle 30 combination is useful in practicing the medical procedure of the preferred embodiment of the present invention. A needle such as that available through Cook Urological Incorporated of Spencer, Ind., as Model No. 090020 may be used.

Figure 2:
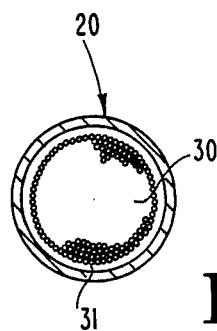
FIG. 2 is an enlarged cross-sectional view of the needle of FIG. 1 with fiber optic bundle disposed therein and taken along line 2—2 of FIG. 1.

FIG. 2 shows the needle 20 and fiber optic bundle 30 of FIG. 1 as it would appear looking proximally from a cross-section taken through the line 2—2 of FIG. 1 from distal tip 24 of the needle 20. Individual glass fibers 31 of the fiber optic bundle 30 are observable. The outer diameter of the fiber optic bundle 30 must be such that it fits easily within the lumen 22 of the needle 20. A fiber optic bundle such as that available from Mitsubishi of Japan.

Figure 3:
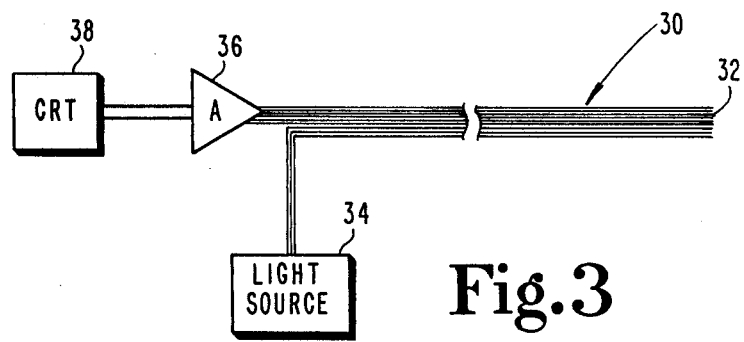
FIG. 3 is a schematic of an operative fiber optic assembly useful in practicing the present invention.

FIG. 3 shows a schematic of the fiber optic bundle 30 connected to a light source 34, an amplifier 36, and a cathode ray tube 38 in the configuration useful in practicing the present invention. The fiber optic bundle 30 comprises a nominal 4,000 individual glass fibers 31 of which about 1 to 1½ percent are used to transmit or pipe light from the light source to the distal end 32 of the fiber optic bundle 30. This light illuminates the selected body cavity, for example, the kidney. The remaining 98.5 to 99 percent of the glass fibers 31 collect and transmit image forming light reflected from the body cavity. The reflected light passes to the amplifier 36 where it is amplified approximately 200 times and displayed on the cathode ray tube 38. In this manner the real images from inside the body are indirectly observable by the human eye.

Figure 4A:
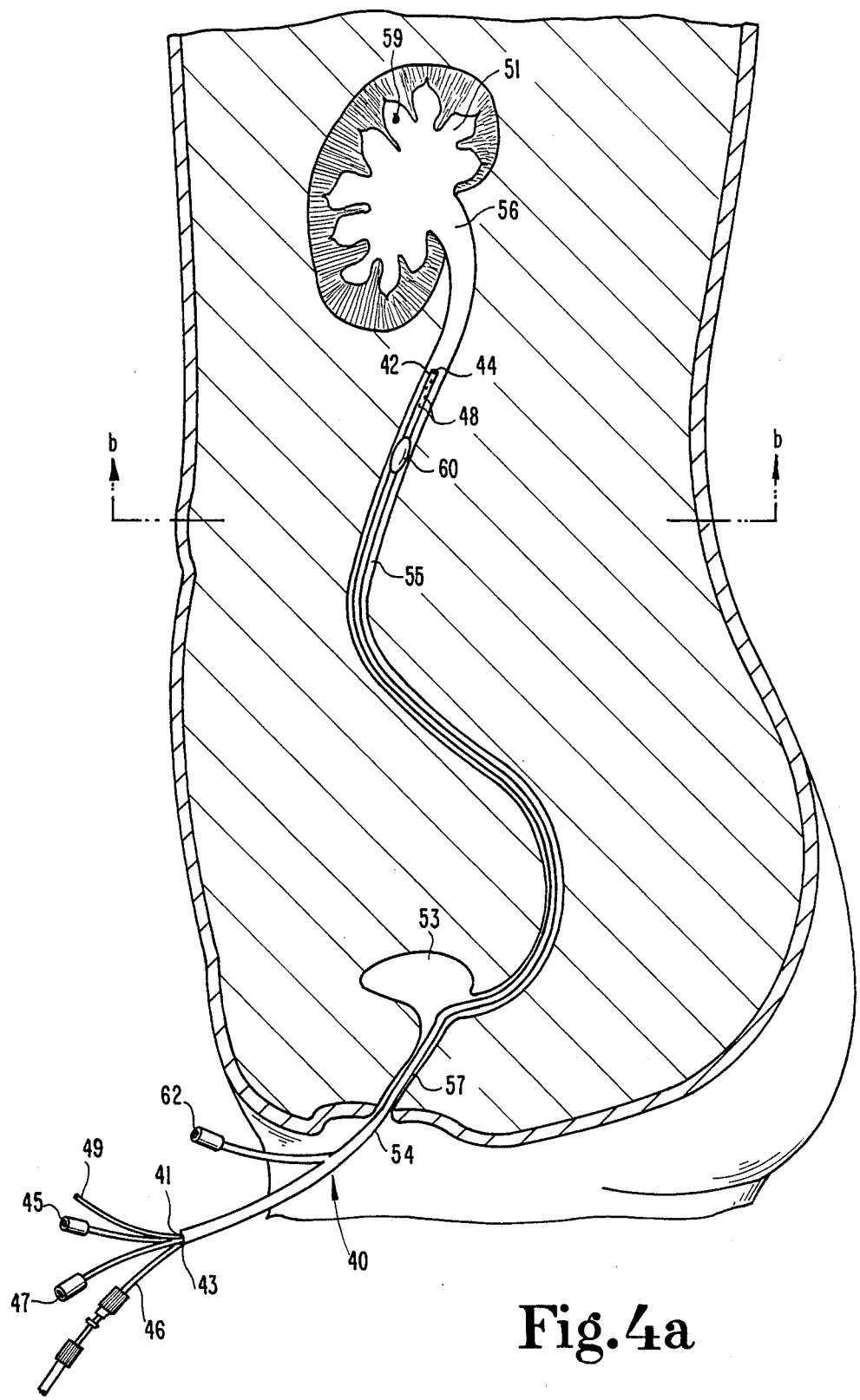
FIG. 4a through FIG. 4e are fragmentary sagittal, median sections through a female pelvis, including the renal system, demonstrating the medical procedure performed according to the present invention.
Figure 4B:
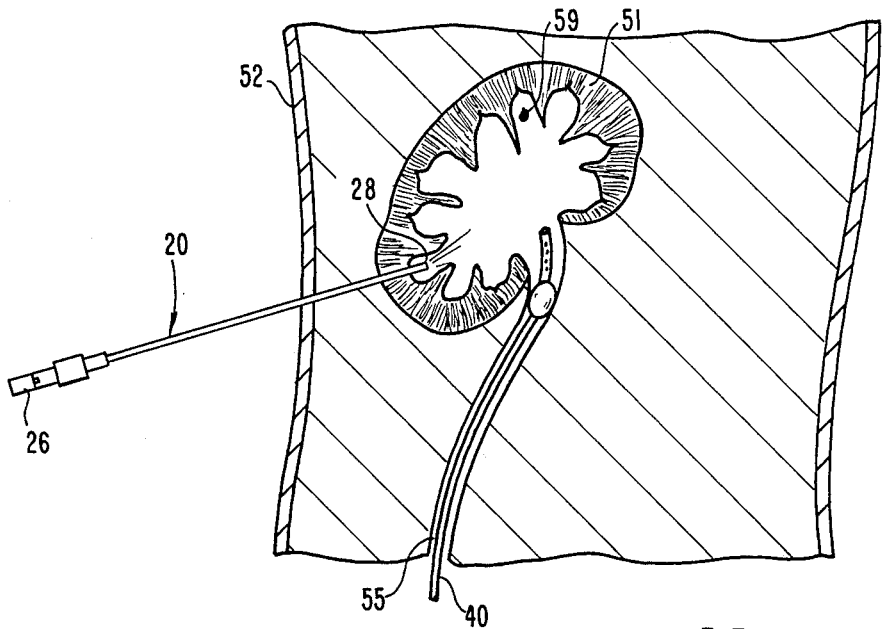
Figure 4C:
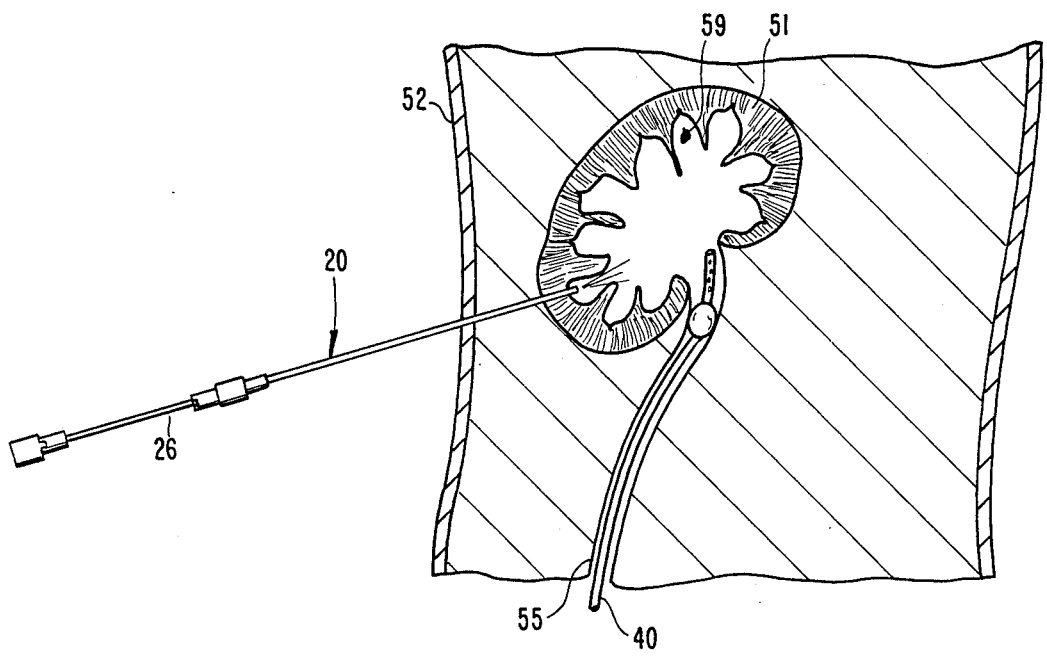

FIGS. 4a through 4e demonstrate a medical procedure performed according to the preferred embodiment of the present invention. A fragmentary, sagittal, median section through a human female pelvis is shown in FIGS. 4a through 4c to portray the medical procedure of the present invention. Exemplary use of a female pelvis is not meant to limit the present invention which is equally applied to human males. FIGS. 4b through 4c are fractional views of the section shown in FIG. 4a, taken proximal of line b-b.

In general, a multi-lumen catheter 40 is advanced through existing anatomical ducts under x-ray (fluoroscope) or ultrasound guidance, just as a ureteral catheter would be passed to the position shown in FIG. 1. At some point of advancement, a small gauge needle 20 with obturating stylet 26 is percutaneously introduced and positioned into the collecting system of the kidney 51, for example, including the renal pelvis and calices. The stylet 26 is then removed and a fiber optic bundle 30 is placed through the needle lumen 22 to observe inside the organ, the kidney 51 in the preferred embodiment. By viewing through the needle 20 and fiber optic bundle 30 assembly shown in FIG. 1, the clinician may observe the end of the catheter 40 as it is advanced into the kidney 51.

FIG. 4a shows a multi-lumen catheter 40 already partially inserted through existing anatomical ducts. Initially, the catheter is inserted from the urethral meatal orifice 54 into the urethra 57, through the bladder 53 and into the ureter 55 with a target location of the kidney 51. The catheter 40 shown is a multi-lumen balloon catheter having an opening 44 at its distal end 42 such that an operative instrument 46 may be inserted through the lumen 43 connecting with the distal opening 44 for the performance of a surgical procedure. For this purpose a multi-lumen catheter 40 such as that available from Cook Urological Incorporated of Spencer, Ind. U.S.A. as a Multi-Lumen Ureteral Catheter is useful. In the present embodiment, the surgical procedure involves removal of a kidney stone 59 from the kidney 51. The operative instrument 46 may be Kim stone forceps as shown in the preferred embodiment, available from Cook Urological Incorporated of Spencer, Ind., as Model No. 011666. Alternate accessory devices may be used for a variety of other surgical procedures. Some of these other devices include 3 or 4 prong grasping forceps; cup, rat-tooth or alligator forceps; loop retrievers; helical or flat-wire stone extractors; electrohydraulic lithotripsy probes; and so forth. The catheter 40 shown has a lumen 47 in communication with side ports 48 for the delivery of fluids, i.e. $CO_2$ gas, various x-ray contrast media, sterile water, sterile saline solution and the like. Another lumen 45 is present for drainage of the irrigation fluids. Still another lumen 41 is present to accept a deflecting wire guide 49 that renders the catheter 40 actively steerable. A wire guide 49 such as that available from Cook Urological Incorporated of Spencer, Ind., as Model No. 738415, may be used for this purpose. The wide variety of functional lumina is made possible since the optic portion of the catheter 40 is remote from the catheter 40, enabling a smaller catheter size or, as in the present case, a greater variety of functional capacities incorporated in a single catheter.

The initial catheter 40 insertion may be accomplished via direction from methods readily known to those skilled in the medical arts. For example, the catheter may be directed to the point shown in FIG. 4a via external guidance under x-ray (fluoroscopic) or ultrasound guidance. Moreover, the catheter may be inserted to various positions either further than that shown in FIG. 4a or less far than that shown under such guidance.

FIG. 4b shows the catheter 40 after it has been advanced into the renal pelvis 56. A needle 20 with an obturating stylet 26 inserted therethrough has been inserted percutaneously and positioned in the collecting system kidney 51.

FIG. 4c shows the needle 20 with the obturating stylet 26 partially removed.

Figure 4D:
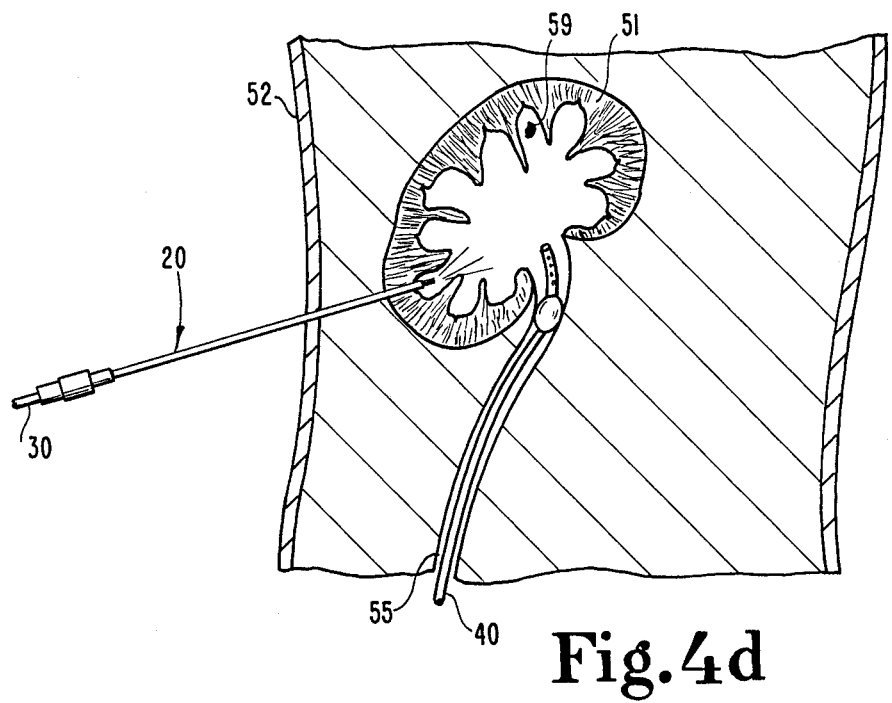

FIG. 4d shows the needle 20 after complete removal of the obturating stylet 26. The fiber optic bundle 30 has now been inserted through the needle's lumen. The inside of the kidney 51, including the stone 59, the intrarenal tissues and the distal end 42 of the catheter 40, is observable via the fiber optic bundle 30. Incoming light is supplied through nominally forty to sixty of the glass fibers 31, illuminating the inside of the kidney 51. Light is reflected from the walls and features inside the kidney and returns by the remaining glass fibers 31 to the amplifier 36 where it is magnified about 200 times. The magnified image is displayed on screen 38 for observation by the clinician. The clinician uses the resulting actual image returned to direct the catheter 40 to its target, the kidney stone 59, using the wire guide 79.

Figure 4E:
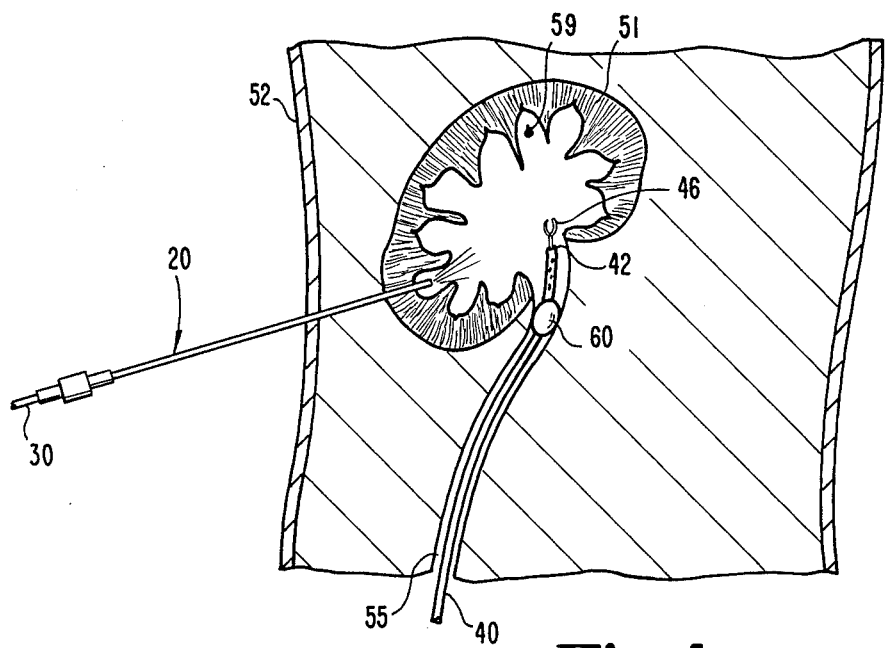

FIG. 4e shows the catheter 40 under such direction. The tip of the multi-lumen catheter 40 is directed to the stone 59. The operative instrument 46 is shown extended relative the distal tip 42 of the catheter 40 and is subsequently manipulated to remove the kidney stone. The balloon 60 may be inflated, if desired. Balloon inflation is accomplished by attaching a source of inflation fluid so that it communicates with lumen 62. Also, the infusion and drainage lumens may be used to administer treatment, if such use is required. After successfully retrieving the stone 59 or performing the requisite procedure, the catheter 40 is withdrawn through the existing anatomical ducts, in this case down the ureter 55, into the bladder 53, through the urethra 57 and out the body via the urethral meatal orifice 54.

Although in the embodiment shown in FIGS. 4a through 4e the needle 20 is inserted after partial insertion of the catheter 40, insertion of the needle 20 before catheter 40 insertion is contemplated as an alternate embodiment of the present invention.

The method of the present invention is not limited to removal of kidney stones and is readily adaptable to medical procedures involving investigation of tumors or suspect lesions, sites of infections or other clinically suspicious areas for investigation or surgical intervention. Surgical intervention, if indicated, is accomplished via the accessory and irrigation lumens of the multi-lumen catheter 40. Adaptation of the present invention for use in any of the above listed methods or other methods should be readily conceived by the ordinarily skilled clinician.

Importantly, the use of the needle 20 with obturating stylet 26 insertable through the needle lumen 22, followed by insertion of the fiber optic bundle 30 is not limited to use with a catheter, single or multi-lumen, and other uses of the needle 20 and fiber optic bundle 30 combination should be readily apparent to the practitioner. Especially, the needle and fiber optic combination is not limited to use in urinary tract applications. The needle/fiber optic assembly may be used to observe any body cavity, whether or not surgical intervention is ultimately indicated. In other words, the needle/fiber optic combination of the present invention may be inserted into an organ for diagnostic purposes apart from use with a catheter or other medical instrument.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. An endoscopic method comprising the steps of:
   A. inserting a medical instrument into the body, said instrument having at least one operative end;
   B. penetrating into the body remote from said instrument with a needle having a lumen;
   C. introducing a fiber optic means through the lumen of said needle, said fiber optic means being also remote from said medical instrument; and,
   D. guiding the operative end of said medical instrument under vision via said remote fiber optic means.

2. The method of claim 1 wherein said penetrating with said needle is accomplished percutaneously.

3. The method of claim 2 additionally comprising the step of:
   E. placing an obturating stylet through the lumen of said needle prior to penetrating with said needle into the body and removing said stylet prior to said introducing said fiber optic means.

4. The method of claim 1 wherein said needle is of 0.049 inch or a smaller outer diameter.

5. The method of claim 4 and further wherein said needle is of 0.039 inch or smaller inner diameter.

6. The method of claim 1 wherein said fiber optic means is of 0.039 inch or less outer diameter.

7. The method of claim 1 wherein said fiber optic means comprises a fiber optic bundle, said fiber optic bundle including approximately 4,000 glass fibers, and wherein approximately 40 of said glass fibers are used to transmit light into the body cavity, and further wherein the remaining said glass fibers are used to return an image from the body cavity to a transmission means.

8. The method of claim 7 wherein said transmission means comprises an amplification means for magnifying the image from the body cavity and a viewing means for viewing the magnified image.

9. The method of claim 8 wherein said viewing means comprises a cathode ray tube.

10. The method of claim 1 and further comprising the step of:
    F. initially directing said medical instrument under external guidance means.

11. The method of claim 10 wherein steps A and F are accomplished before steps B and C, and further wherein steps B and C take place before step D.

12. The method of claim 10 wherein said external guidance means is a flouroscope.

13. The method of claim 10 wherein said external guidance means utilizes ultrasound.

14. The method of claim 1 wherein said inserting of said medical instrument is through existing anatomical ducts.

15. The method of claim 1 wherein said medical instrument is a catheter.

16. The method of claim 15 wherein the catheter is a multi-lumen catheter.

17. The method of claim 14 wherein said inserting of said medical instrument is through the urethra.

18. The method of claim 16 wherein said multi-lumen catheter comprises a lumen for delivery of fluids and a lumen for delivery of operative accessory devices.

19. The method of claim 18 and further wherein said multi-lumen catheter also comprises a lumen for drainage, a balloon, a lumen for inflating the balloon, and a lumen for steering means to render the catheter steerable.

20. An apparatus for performing a medical procedure inside the body comprising:
    a needle, said needle having a lumen;
    an obturating stylet insertable within the lumen of said needle and removable after said needle is positioned;
    a fiber optic means insertable through the lumen of said needle after removal of said obturating stylet; and
    a medical instrument having at least one operative end, said medical instrument being remotely guidable under vision via said fiber optic means.

21. The apparatus of claim 20 wherein said needle is of 0.049 inch or a smaller outer diameter.

22. The apparatus of claim 21 wherein the inner diameter of said needle is of 0.039 inch or smaller.

23. The apparatus of claim 20 wherein the fiber optic means comprises a fiber optic bundle, said fiber optic bundle including approximately 4,000 glass fibers, and wherein approximately 40 of said glass fibers are used to transmit light into the body cavity, and further wherein the remaining said glass fibers are used to transmit an image from the body cavity to a transmission means.

24. The apparatus of claim 23 wherein said transmission means comprises an amplification means for magnifying the image from the body cavity and a viewing means for viewing the magnified image.

25. The apparatus of claim 24 wherein said viewing means comprises a cathode ray tube.

* * * * *

UNITED STATES PATENT AND TRADEMARK OFFICE
CERTIFICATE OF CORRECTION

PATENT NO. : 4,945,895

DATED : August 7, 1990

INVENTOR(S) : Kazuo Takai, et al.

It is certified that error appears in the above-identified patent and that said Letters Patent is hereby corrected as shown below:

TITLE PAGE, block [75], please change "Genty" to --Gentry--.

In column 1, line 19, please change "Where" to --where--.

In column 2, line 20, please change "he" to --be--.

In column 3, line 47, please change "Wherein" to --wherein--.

In column 3, line 53, please change "folloWing" to --following--.

In column 6, line 15, please change "With" to --with--.

In column 6, line 43, please change "Withdrawn" to --withdrawn--.

Signed and Sealed this

Seventeenth Day of March, 1992

Attest:

HARRY F. MANBECK, JR.

*Attesting Officer*     *Commissioner of Patents and Trademarks*